United States Patent
Ribble et al.

(10) Patent No.: US 9,861,550 B2
(45) Date of Patent: Jan. 9, 2018

(54) ADVERSE CONDITION DETECTION, ASSESSMENT, AND RESPONSE SYSTEMS, METHODS AND DEVICES

(71) Applicant: Hill-Rom Services, Inc., Batesville, IN (US)

(72) Inventors: David Ribble, Indianapolis, IN (US); Michelle McCleerey, Raleigh, NC (US); Eric Agdeppa, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 652 days.

(21) Appl. No.: 13/900,209

(22) Filed: May 22, 2013

(65) Prior Publication Data

US 2013/0317399 A1    Nov. 28, 2013

Related U.S. Application Data

(60) Provisional application No. 61/650,436, filed on May 22, 2012.

(51) Int. Cl.
| | |
|---|---|
| *A61H 7/00* | (2006.01) |
| *G06F 19/00* | (2011.01) |
| *G08B 21/02* | (2006.01) |

(52) U.S. Cl.
CPC .......... *A61H 7/001* (2013.01); *G06F 19/3431* (2013.01); *G06F 19/3481* (2013.01); *G08B 21/02* (2013.01); *F04C 2270/0421* (2013.01)

(58) Field of Classification Search
CPC ..... A61B 5/447; A61H 7/001; G09F 19/3431; G09F 19/3481
See application file for complete search history.

(56) References Cited

U.S. PATENT DOCUMENTS

| | | | |
|---|---|---|---|
| 2,194,809 A | 3/1940 | Powell, Jr. | |
| 3,325,799 A | 6/1967 | Farris | |
| 3,631,438 A | 12/1971 | Lewin | |
| 3,644,950 A | 2/1972 | Lindsay, Jr. | |
| 3,727,606 A | 4/1973 | Sielaff | |
| 3,836,900 A | 9/1974 | Mansfield | |
| 3,996,928 A | 12/1976 | Marx | |

(Continued)

FOREIGN PATENT DOCUMENTS

| | | |
|---|---|---|
| EP | 2417908 A1 | 2/2012 |
| JP | 06315424 A2 | 11/1994 |
| WO | 2008/096307 A1 | 8/2008 |
| WO | 2009/095877 A2 | 8/2009 |

OTHER PUBLICATIONS

L. Tarassenko et al., "Biosign™: Multi-Parameter Monitoring for Early Warning of Patient Deterioration", (6 pages).

(Continued)

*Primary Examiner* — Steven Douglas
*Assistant Examiner* — Kathrynn Lyddane
(74) *Attorney, Agent, or Firm* — Barnes & Thornburg LLP

(57) ABSTRACT

A method includes receiving an input indicative of at least one factor that contributes to the development of pressure ulcers; determining a risk score as a function of the input; comparing the risk score to a previous risk score; and at least one of activating a therapy configured to reduce the magnitude of the factor and notifying a caregiver if the risk score is greater than the previous risk score.

27 Claims, 9 Drawing Sheets

(56) References Cited

U.S. PATENT DOCUMENTS

| | | | |
|---|---|---|---|
| 4,146,885 A | 3/1979 | Lawson, Jr. | |
| 4,195,287 A | 3/1980 | McCoy et al. | |
| 4,245,651 A | 1/1981 | Frost | |
| 4,422,458 A | 12/1983 | Kravath | |
| 4,481,686 A | 11/1984 | Lacoste | |
| 4,483,029 A | 11/1984 | Paul | |
| 4,485,505 A | 12/1984 | Paul | |
| 4,525,885 A | 7/1985 | Hunt et al. | |
| 4,554,930 A | 11/1985 | Kress | |
| 4,559,656 A | 12/1985 | Foster | |
| 4,564,965 A | 1/1986 | Goodwin | |
| 4,595,023 A | 6/1986 | Bonnet | |
| 4,602,643 A | 7/1986 | Dietz | |
| 4,637,083 A | 1/1987 | Goodwin | |
| 4,657,026 A | 4/1987 | Tagg | |
| 4,677,857 A | 7/1987 | Feldmann | |
| 4,681,098 A | 7/1987 | Lee | |
| 4,694,520 A | 9/1987 | Paul et al. | |
| 4,757,825 A | 7/1988 | Diamond | |
| 4,799,276 A | 1/1989 | Kadish | |
| 4,838,309 A | 6/1989 | Goodwin | |
| 4,889,131 A | 12/1989 | Salem et al. | |
| 4,934,468 A | 6/1990 | Koerber, Sr. et al. | |
| 4,935,968 A | 6/1990 | Hunt et al. | |
| 4,942,635 A | 7/1990 | Hargest et al. | |
| 4,949,412 A | 8/1990 | Goode | |
| 4,949,414 A | 8/1990 | Thomas et al. | |
| 4,967,195 A | 10/1990 | Shipley | |
| 4,971,065 A | 11/1990 | Pearce | |
| 5,010,772 A | 4/1991 | Bourland et al. | |
| 5,052,067 A | 10/1991 | Thomas et al. | |
| 5,057,819 A | 10/1991 | Valenti | |
| 5,060,174 A | 10/1991 | Gross | |
| 5,101,828 A | 4/1992 | Welkowitz et al. | |
| 5,117,518 A | 6/1992 | Schild | |
| 5,170,364 A | 12/1992 | Gross et al. | |
| 5,182,826 A | 2/1993 | Thomas et al. | |
| 5,184,112 A | 2/1993 | Gusakov | |
| 5,276,432 A | 1/1994 | Travis | |
| 5,283,735 A | 2/1994 | Gross et al. | |
| 5,539,942 A | 7/1996 | Melou | |
| 5,561,412 A | 10/1996 | Novak et al. | |
| 5,664,270 A | 9/1997 | Bell et al. | |
| 5,738,102 A | 4/1998 | Lemelson | |
| 5,794,288 A | 8/1998 | Soltani et al. | |
| 5,815,864 A | 10/1998 | Sloop | |
| 5,817,146 A | 10/1998 | Augustine | |
| 5,829,081 A | 11/1998 | Pearce | |
| 5,873,137 A | 2/1999 | Yavets-Chen | |
| 5,934,280 A | 8/1999 | Viard et al. | |
| 5,964,720 A | 10/1999 | Pelz | |
| 5,970,789 A | 10/1999 | Meyer et al. | |
| 6,009,580 A | 1/2000 | Caminade et al. | |
| 6,011,477 A | 1/2000 | Teodorescu et al. | |
| 6,034,526 A | 3/2000 | Montant et al. | |
| 6,067,019 A | 5/2000 | Scott | |
| 6,067,466 A | 5/2000 | Selker et al. | |
| 6,079,068 A | 6/2000 | Viard | |
| 6,094,762 A | 8/2000 | Viard et al. | |
| 6,208,250 B1 | 3/2001 | Dixon et al. | |
| 6,212,718 B1 | 4/2001 | Stolpmann et al. | |
| 6,493,568 B1 | 12/2002 | Bell et al. | |
| 6,560,804 B2 | 5/2003 | Wise et al. | |
| 6,721,980 B1 | 4/2004 | Price et al. | |
| 6,739,006 B2 | 5/2004 | Borders et al. | |
| 6,984,207 B1 | 1/2006 | Sullivan et al. | |
| 7,031,857 B2 | 4/2006 | Tarassenko et al. | |
| 7,077,810 B2 | 7/2006 | Lange et al. | |
| 7,127,948 B2 | 10/2006 | Tavares et al. | |
| 7,183,930 B2 | 2/2007 | Basir et al. | |
| 7,242,306 B2 | 7/2007 | Wildman et al. | |
| 7,242,308 B2 | 7/2007 | Ulrich et al. | |
| 7,245,956 B2 | 7/2007 | Matthews et al. | |
| 7,248,933 B2 | 7/2007 | Wildman | |
| 7,253,366 B2 | 8/2007 | Bhai | |
| 7,289,844 B2 | 10/2007 | Misczynski et al. | |
| 7,296,312 B2 | 11/2007 | Menkedick et al. | |
| 7,304,580 B2 | 12/2007 | Sullivan et al. | |
| 7,306,564 B2 | 12/2007 | Nakatani et al. | |
| 7,314,451 B2 | 1/2008 | Halperin et al. | |
| 7,315,535 B2 | 1/2008 | Schuman | |
| 7,319,386 B2* | 1/2008 | Collins, Jr. | A61B 5/1115 340/286.07 |
| 7,330,127 B2 | 2/2008 | Price et al. | |
| 7,443,303 B2 | 10/2008 | Spear et al. | |
| 7,472,956 B2 | 1/2009 | Makhsous et al. | |
| 7,515,059 B2 | 4/2009 | Price et al. | |
| 7,629,890 B2 | 12/2009 | Sullivan et al. | |
| 7,973,666 B2 | 7/2011 | Petrosenko et al. | |
| 2001/0004778 A1 | 6/2001 | Heimbrock et al. | |
| 2003/0144829 A1 | 7/2003 | Geatz et al. | |
| 2004/0111045 A1 | 6/2004 | Sullivan et al. | |
| 2005/0027416 A1 | 2/2005 | Basir et al. | |
| 2005/0124864 A1 | 6/2005 | Mack et al. | |
| 2005/0165284 A1 | 7/2005 | Gefen | |
| 2005/0168341 A1 | 8/2005 | Reeder et al. | |
| 2005/0190062 A1 | 9/2005 | Sullivan et al. | |
| 2005/0190068 A1 | 9/2005 | Gentry et al. | |
| 2005/0273940 A1 | 12/2005 | Petrosenko | |
| 2006/0101581 A1 | 5/2006 | Blanchard et al. | |
| 2006/0169282 A1 | 8/2006 | Izumi et al. | |
| 2006/0179952 A1 | 8/2006 | Tavares et al. | |
| 2007/0118054 A1 | 5/2007 | Pinhas et al. | |
| 2007/0210917 A1 | 9/2007 | Collins, Jr. et al. | |
| 2007/0247316 A1 | 10/2007 | Wildman et al. | |
| 2008/0060138 A1 | 3/2008 | Price et al. | |
| 2008/0094207 A1 | 4/2008 | Collins, Jr. et al. | |
| 2008/0095156 A1 | 4/2008 | Schuman | |
| 2008/0096307 A1 | 4/2008 | Basol | |
| 2008/0114260 A1 | 5/2008 | Lange et al. | |
| 2008/0146892 A1 | 6/2008 | LeBoeuf et al. | |
| 2008/0269625 A1 | 10/2008 | Halperin et al. | |
| 2008/0275349 A1* | 11/2008 | Halperin | A61B 5/0205 600/484 |
| 2008/0281170 A1 | 11/2008 | Eshelman et al. | |
| 2009/0054735 A1 | 2/2009 | Higgins et al. | |
| 2009/0062623 A1 | 3/2009 | Cohen | |
| 2009/0069642 A1 | 3/2009 | Gao et al. | |
| 2009/0070939 A1* | 3/2009 | Hann | A61B 5/11 5/652.1 |
| 2009/0088606 A1 | 4/2009 | Chuddihy et al. | |
| 2009/0093686 A1 | 4/2009 | Hu et al. | |
| 2009/0095877 A1 | 4/2009 | Poo | |
| 2009/0105550 A1* | 4/2009 | Rothman | G06F 19/3431 600/300 |
| 2009/0163774 A1 | 6/2009 | Thatha et al. | |
| 2009/0216556 A1 | 8/2009 | Martin et al. | |
| 2009/0326339 A1 | 12/2009 | Horvitz | |
| 2010/0099954 A1 | 4/2010 | Dickinson et al. | |
| 2010/0170043 A1 | 7/2010 | Young et al. | |
| 2010/0174198 A1 | 7/2010 | Young et al. | |
| 2011/0010014 A1 | 1/2011 | Oexman et al. | |
| 2011/0068935 A1 | 3/2011 | Riley et al. | |
| 2011/0163875 A1 | 7/2011 | Poulos et al. | |
| 2011/0301440 A1* | 12/2011 | Riley | A61B 5/02055 600/301 |
| 2012/0174322 A1 | 7/2012 | Skinner et al. | |
| 2013/0246088 A1* | 9/2013 | Huster | G06Q 10/0635 705/2 |
| 2013/0249695 A1* | 9/2013 | Hann | G08B 21/0438 340/573.7 |

OTHER PUBLICATIONS

C. P. Subbe, et al., "Validation of a modified Early Warning Score in medical admissions", *Q J Med* 2001: 94: 521-526.

Marilyn Hravnak et al., "Defining the Incidence of Cardiorespiratory Instability in Patients in Step-down Units Using an Electronic Integrated Monitoring System", *Arch Intern Med*, vol. 168 (No. 12), Jun. 23, 2008, 1300-1308.

L. Tarassenko, et al., "Integrated monitoring and analysis for early warning of patient deterioration", *British Journal of Anasthesia*, May 17, 2006, (5 pages).

(56) References Cited

OTHER PUBLICATIONS

"Visensia", *OBS Medical Ltd*. (4 pages).
Coba V. Rubinfeld I, et al., "Can the Visensia Index Score Predict Mortality in High Risk Injured Patients?", (1 page).
European Search Report for Application # 13168776.6 dated Feb. 18, 2014; Place of search—Munich; Date—Feb. 12, 2014.
Sufi et al., A mobile phone based intelligent scoring approach for assessment of critical illness, Technology and Applications in Biomedicine, 2008. ITAB 2008. International Conference on, IEEE, Piscataway, NJ, USA, May 30, 2008, pp. 290-293, XP031289425.
European search report from EP 10 17 6765 dated Feb. 16, 2011, 11 pages.

* cited by examiner

ADVERSE CONDITION DETECTION, ASSESSMENT, AND RESPONSE SYSTEMS, METHODS AND DEVICES

This disclosure claims priority to U.S. Provisional Application Ser. No. 61/650,436, filed on May 22, 2012 and titled ADVERSE CONDITION DETECTION, ASSESSMENT, AND RESPONSE SYSTEMS, METHODS AND DEVICES, the contents of which are incorporated herein by reference.

BACKGROUND OF THE DISCLOSURE

This disclosure relates generally to adverse condition detection, assessment, and response systems, devices and methods. More particularly, but not exclusively, one contemplated embodiment relates to a system configured to monitor for physiological factors that contribute to skin breakdown, assess the likelihood of skin breakdown, and take appropriate action to prevent skin breakdown. While various systems have been developed, there is still room for improvement. Thus, a need persists for further contributions in this area of technology.

SUMMARY OF THE DISCLOSURE

In contemplated embodiment, a method comprises receiving an input indicative of a factor that contribute to the development of pressure ulcers; comparing the input to a predetermined threshold; and if the input exceeds the threshold, notifying a caregiver that a pressure ulcer may develop.

In another contemplated embodiment, a method comprises receiving an input indicative of a factor that contribute to the development of pressure ulcers; comparing the input to a predetermined threshold; and if the input exceeds the threshold, activating a therapy configured to reduce the magnitude of the input.

In another contemplated embodiment, a method comprises receiving an input indicative of a factor that contribute to the development of pressure ulcers; determining a Braden score of a person as a function of the input; comparing the Braden score to a predetermined threshold; and if the input exceeds the threshold, activating a therapy configured to reduce the magnitude of the input.

In another contemplated embodiment, a method comprises receiving a first input indicative of a factor that contribute to the development of pressure ulcers; receiving a second input indicative of a factor that contribute to the development of pressure ulcers a predetermined time after receiving the first input; determining the difference between the first input and the second input; if the difference indicates an increase in the factor that contributes to the development of pressure ulcers, activating a therapy configured to reduce the magnitude of the factor.

In another contemplated embodiment, a method comprises receiving a first input indicative of a factor that contribute to the development of pressure ulcers; receiving a second input indicative of a factor that contribute to the development of pressure ulcers a predetermined time after receiving the first input; determining a first Braden score as a function of the first input; determining a second Braden score as a function of the second input; comparing the first Braden score to the second Braden score; and if the first Braden score is less than the second Braden score, activating a therapy configured to reduce the magnitude of the factor.

In another contemplated embodiment, a method comprises receiving a first input indicative of a factor that contribute to the development of pressure ulcers; receiving a second input indicative of a factor that contribute to the development of pressure ulcers a predetermined time after receiving the first input; determining a first Braden score as a function of the first input; determining a second Braden score as a function of the second input; comparing the first Braden score to the second Braden score; and if the first Braden score is less than the second Braden score, notify a caregiver.

In another contemplated embodiment, a method comprises receiving an first input indicative of a characteristic of a patient; receiving a second input indicative of at least one factor that contributes to the development of pressure ulcers, wherein at least one of the at least one factor is ignored as a function of the first input; comparing the second input to a predetermined threshold; if the difference indicates an increase in the factor that contributes to the development of pressure ulcers, at least one of activating a therapy configured to reduce the magnitude of the factor and notifying a caregiver.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
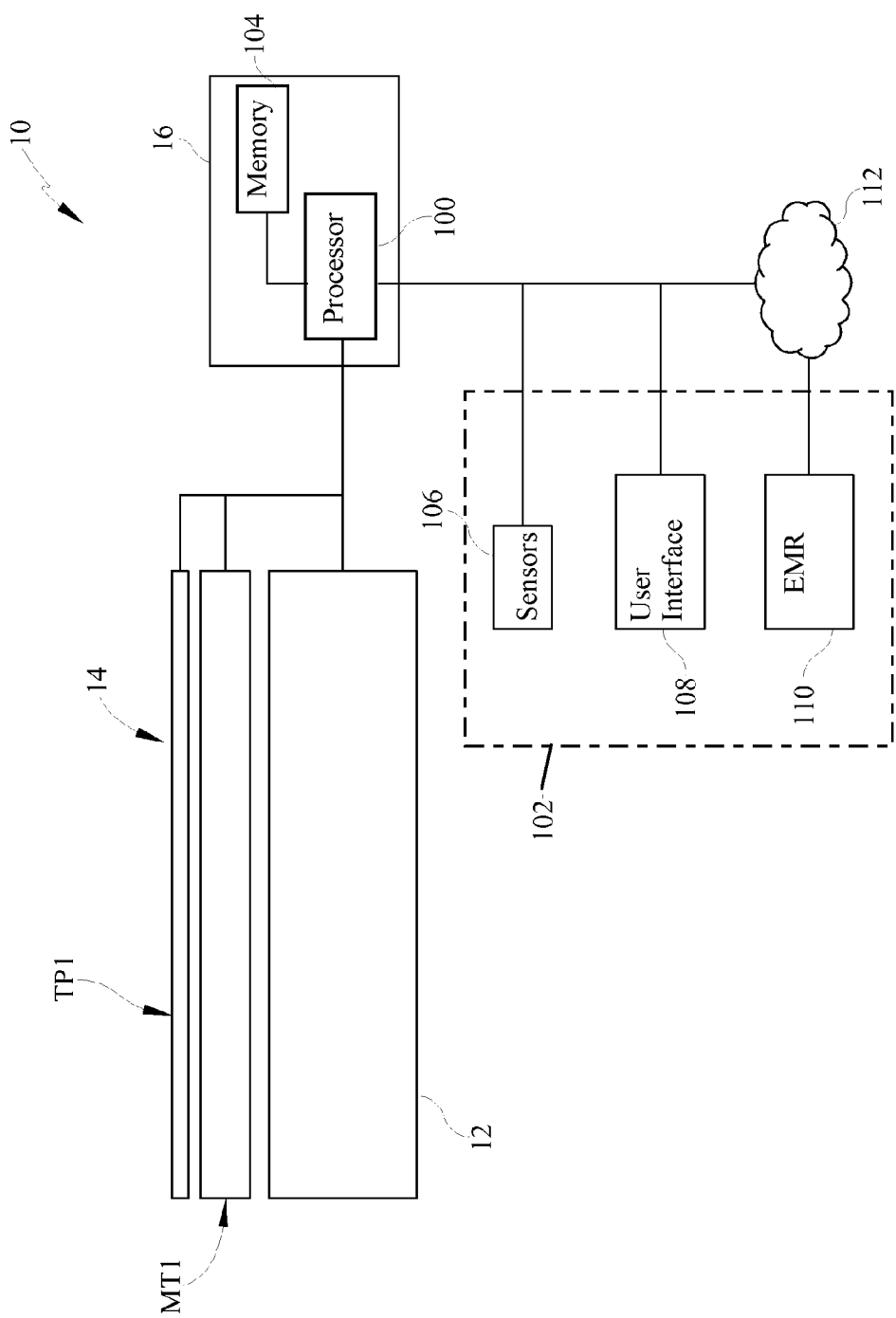
FIG. 1 is a diagrammatic view of adverse condition detection, assessment, and response system including a person support apparatus, a person support surface, and a control system according to one contemplated embodiment of the disclosure.
Figure 2:
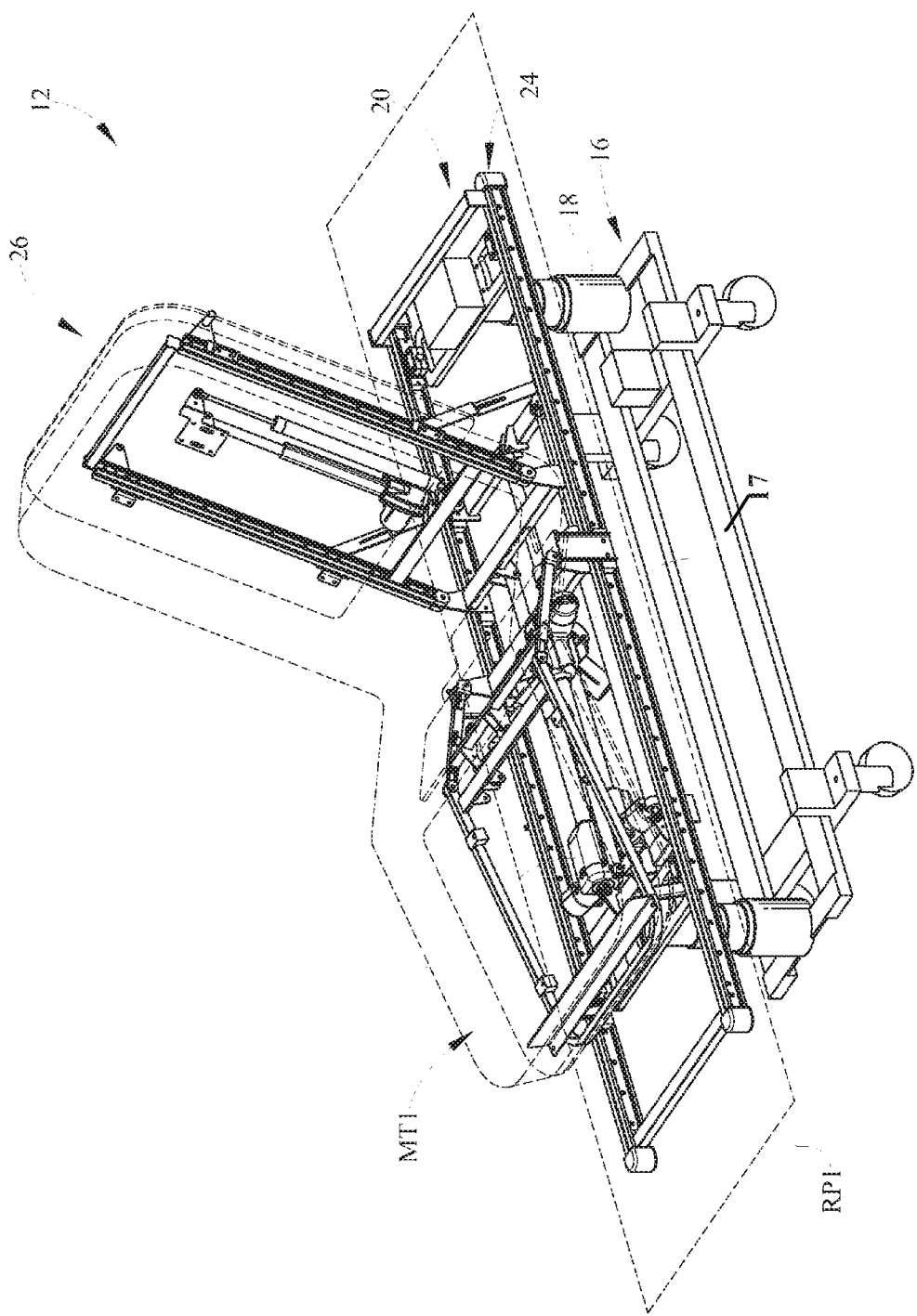
FIG. 2 is a side perspective view of the person support apparatus of FIG. 1 showing the various components of the upper and lower frame.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

FIG. 1 shows adverse condition detection, assessment, and response system 10 according to one contemplated embodiment. The system 10 is configured to monitor physiological factors that can contribute to skin breakdown and the development of pressure ulcers, provide decision support that evaluates what response, if any, is appropriate upon detecting or predicting the occurrence of such a condition, and implement an intervention to address those factors and protect the person's skin from damage. The factors the system 10 measures include, but are not limited to, interface pressure, skin temperature, skin moisture, incontinence, degree and presence of tissue damage or pressure ulcers, lack of motion (i.e., not adjusting their position), lack of activity (i.e., not leaving the person support structure), amount of shear, amount of friction, and the type of person support surface being used. The system can detect both a location and duration of the factor (i.e., what body part experienced excessive pressure and for how long). The system 10 could periodically or continuously monitor the factors. Sensors used to measure the factors may be coupled to a person support apparatus, included in a person support surface, integrated into linens or garments or underpads, or worn by the patient, and can connect wirelessly to the system 10.

The system 10 may be in communication with the emergency medical record (EMR) or other care facility record or database system and receive information necessary to determine the person's risk for skin breakdown or other factors that would influence the caregiver's treatment decision. In one example, the system 10 receives information from the EMR including, but not limited to, the person's medical history, medical diagnosis, medications, Braden score, and risk analyses. In another example, the system 10 receives information from the institutional care protocol, which defines the care that should be given to a patient in order to help prevent skin breakdown. The care protocol can include information, such as, when a specialty person support surface needs to be used, when a therapy should be used, when a catheter should be used, the frequency at which the patient should be turned, and other care procedures.

The system 10 can respond to the detected factors that exceed a predetermined threshold by activating a therapy, such as, targeted cooling, heat and moisture regulation, patient turning, and other therapies, or notifying a caregiver and requesting that a caregiver perform some actions, such as, reposition at least a portion of the patient, apply a salve or pH neutralizing solution, or other care protocol procedures. The system 10 can also provide information to the EMR or other care facility database or record system for compliance reporting and charting.

The system 10 includes a person support apparatus 12, a person support surface 14, a fluid supply FS1, and a control system 16. In some contemplated embodiments, the person support apparatus 12 is a hospital bed frame and the person support surface 14 is supported thereon. In other contemplated embodiments, the person support apparatus 12 can be a stretcher, an operating room table, or other person supporting structure. The person support apparatus 12 includes a lower frame 17, supports 18 or lift mechanisms 18 coupled to the lower frame 17, and an upper frame 20 movably supported above the lower frame 17 by the supports 18. The lift mechanisms 18 are configured to raise and lower the upper frame 20 with respect to the lower frame 17 and move the upper frame 20 between various orientations, such as, Trendellenburg and reverse Trendellenburg.

Figure 3:
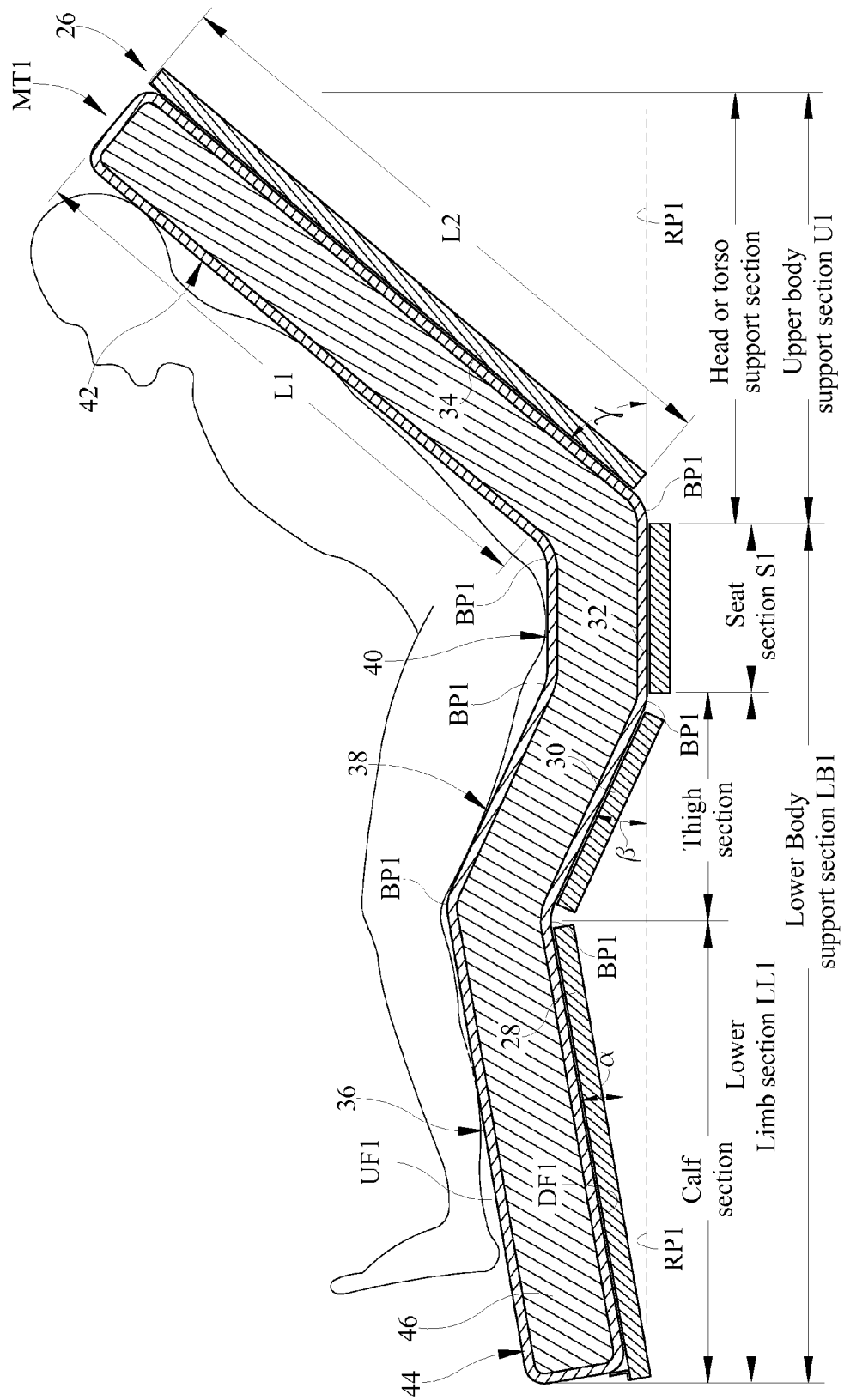
FIG. 3 is a side cross-sectional view of the person support surface of FIG. 1 showing the various sections of the mattress and how they correspond to the sections of the upper frame that support the mattress.
Figure 4:
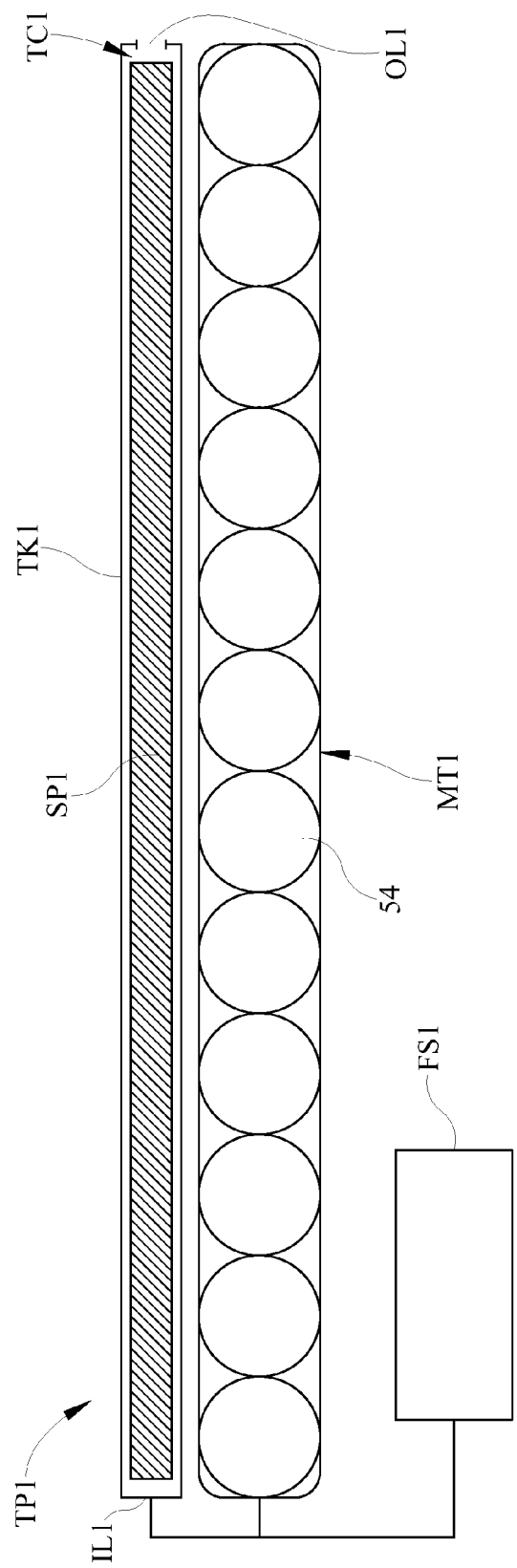
FIG. 4 is a diagrammatic view of the person support surface of FIG. 1 showing the mattress, topper, and fluid supply.

The upper frame 20 includes an upper frame base 24 and a deck 26 coupled to the upper frame base 24. The deck 26 includes a calf section 28, a thigh section 30, a seat section 32, and a head and torso section 34 as shown in FIG. 3. The calf section 28 and the thigh section 30 define a lower limb support section LL1. The head and torso section 34 define an upper body support section U1. The seat section 32 defines the seat section S1. The calf section 28, the thigh section 30, and the seat section 32 define a lower body support section LB1. At least the calf section 28, the thigh section 30, and the head and torso section 34 are movable with respect to one another and/or the upper frame base 24. In some contemplated embodiments, the calf section 28, the thigh section 30, the seat section 32, and the head and torso section 34 cooperate to move the person support apparatus 12 between an substantially planar or lying down configuration and a chair configuration. In some contemplated embodiments, the calf section 28, the thigh section 30, the seat section 32, and the head and torso section 34 cooperate to move the person support apparatus 12 between a substantially planar or lying down configuration and an angled or reclined configuration. In some contemplated embodiments, the head and torso section 34 is moved such that it is at an angle of at least about 30° with respect to a reference plane RP1 passing through the upper frame 20.

The person support surface 14 is configured to support a person thereon and move with the deck 20 between the various configurations. The person support surface 14 includes a calf portion 36, a thigh portion 38, a seat portion 40, and a head and torso portion 42 as shown in FIG. 3, which is supported on corresponding sections of the deck 26. In one contemplated embodiment, the deck sections help move and/or maintain the various portions of the mattress MT1 at angles $\alpha$, $\beta$ and $\gamma$ with respect to the reference plane RP1.

Figure 5:
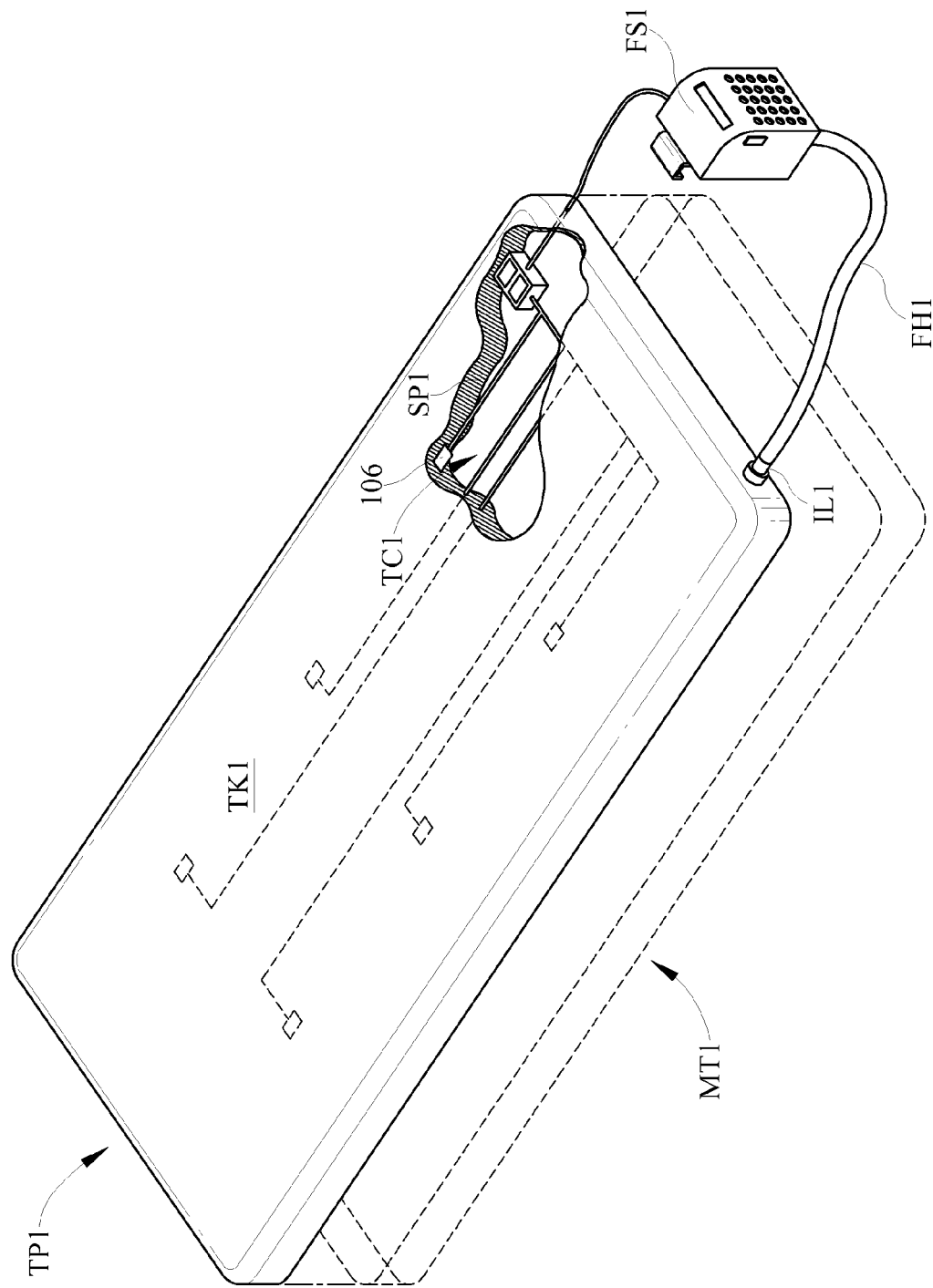
FIG. 5 is a perspective side view of the person support surface showing the sensors in coupled to the topper.
Figure 6:
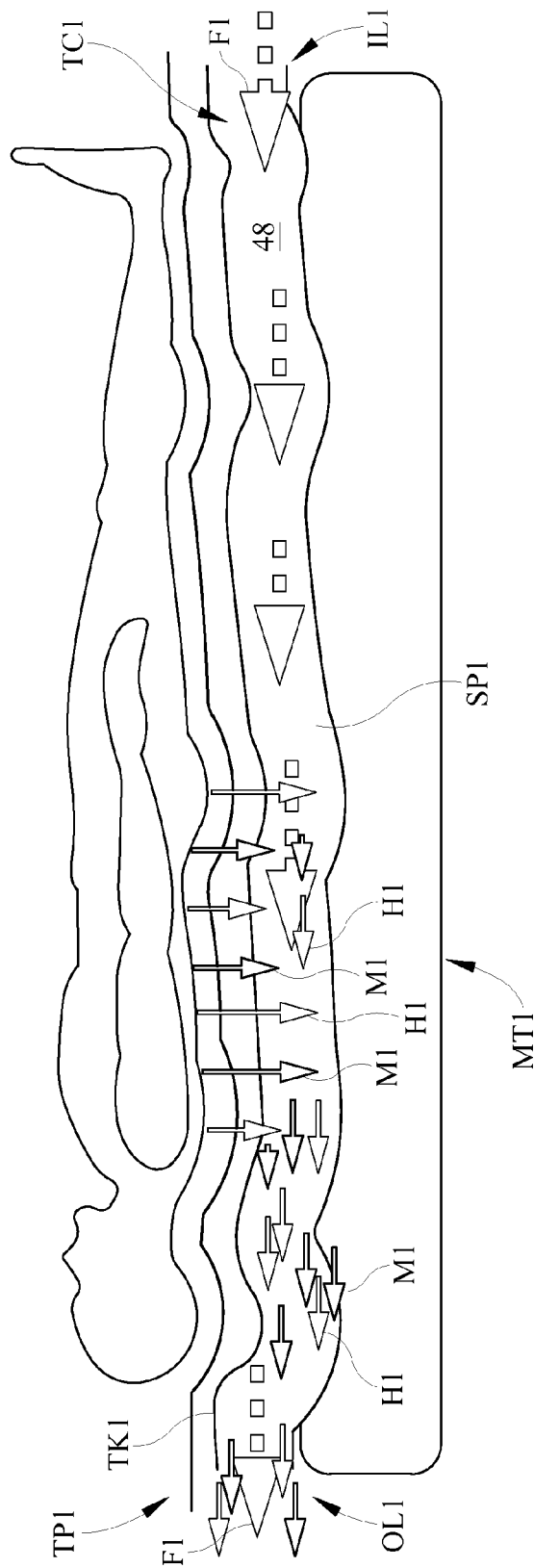
FIG. 6 is a diagrammatic side view of a low air loss topper on a mattress.
Figure 7:
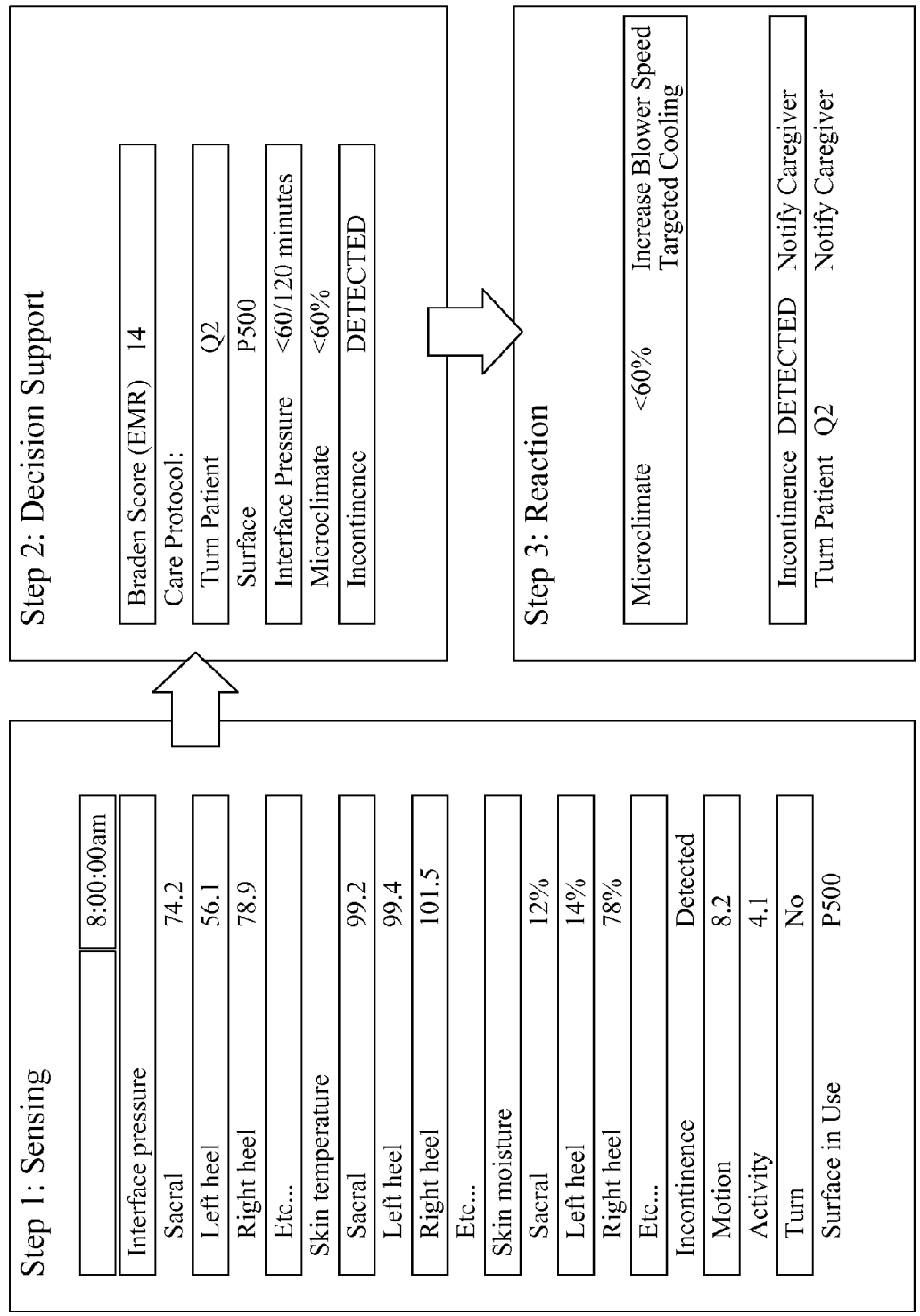
FIG. 7 is a flow chart showing a table of information that is received, a decision support table derived from the information, and a reaction table listing possible interventions.
Figure 8:
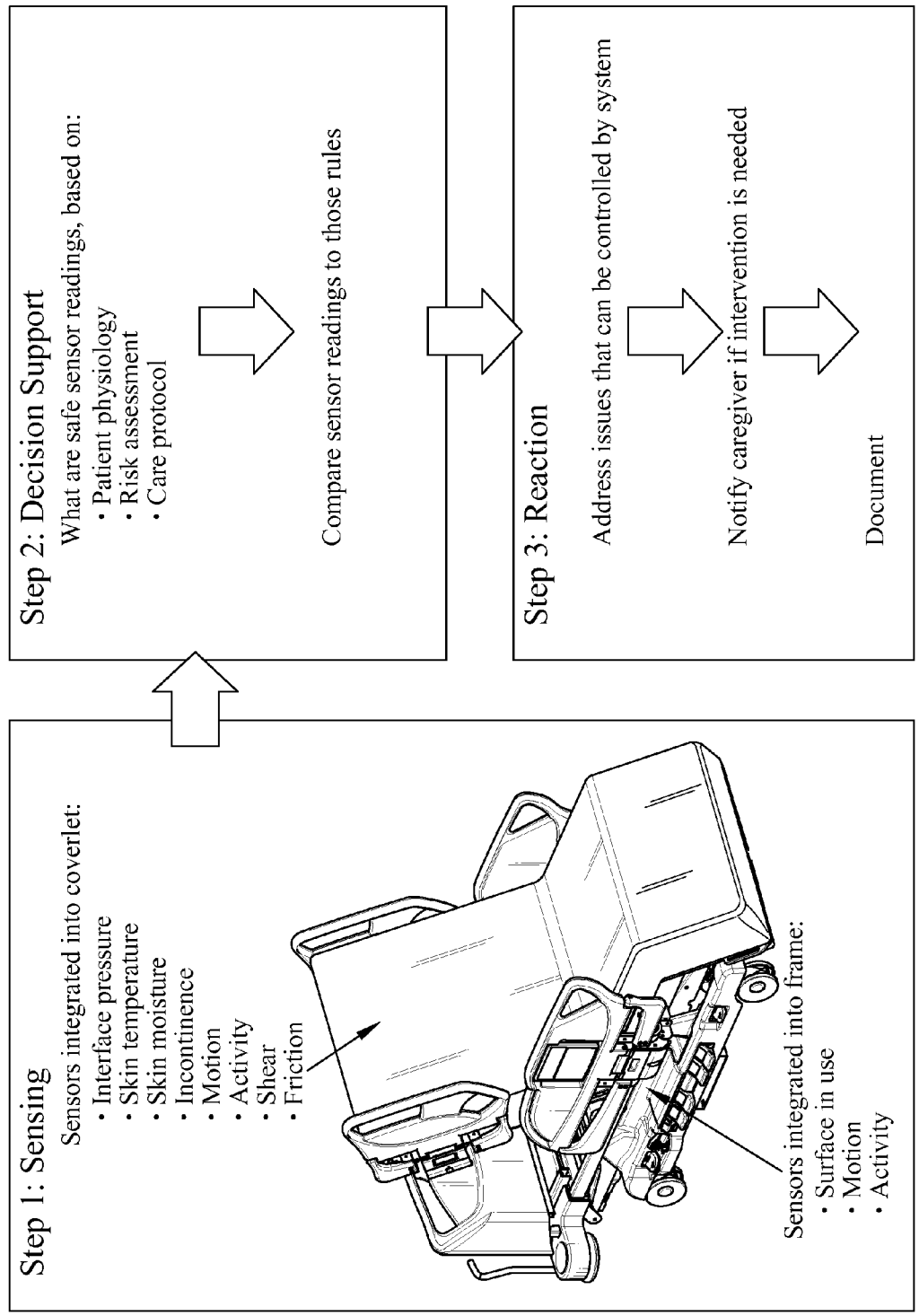
FIG. 8 is a flow chart showing a table of information that is received, a decision support table derived from the information, and a reaction table listing possible interventions according to another contemplated embodiment.
Figure 9:
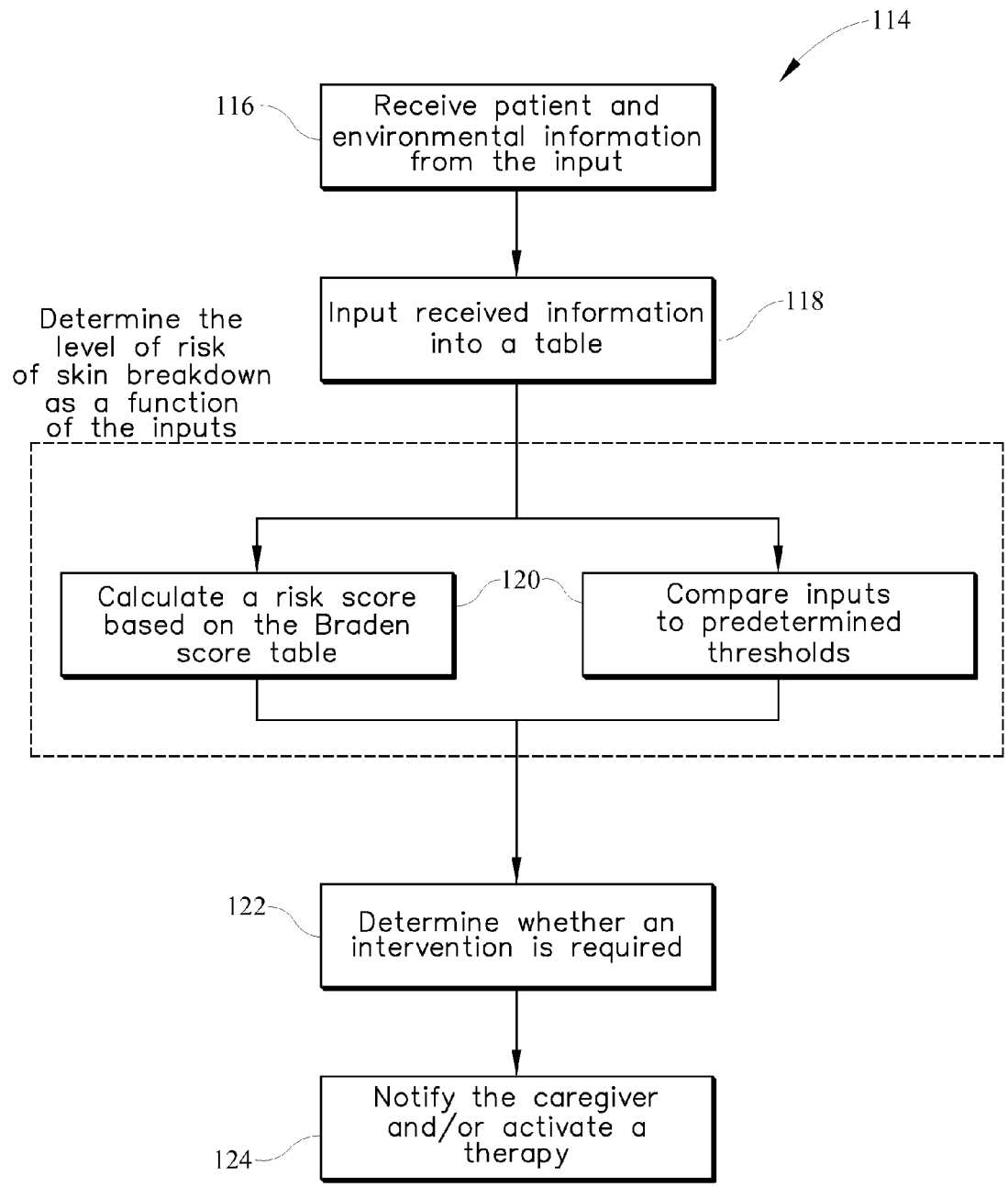
FIG. 9 is a flow chart of a procedure for monitor for physiological factors that contribute to skin breakdown, assess the likelihood of skin breakdown, and take appropriate action to prevent skin breakdown.

The person support surface 14 includes a mattress MT1 and a heat and moisture regulating topper TP1. In some contemplated embodiments, a pressure mapping mat (not shown) is positioned on the mattress MT1 or topper TP1 or incorporated therein. In some contemplated embodiments, the mattress MT1 is a non-powered (static) mattress. In some contemplated embodiments, the mattress MT1 is a powered (dynamic) mattress configured to receive fluid from a fluid supply FS1 as shown in FIG. 5. In some contemplated embodiments, the mattress MT1 is a consumer mattress.

The mattress MT1 includes a mattress cover 44 and a mattress core 46 enclosed by the mattress cover 44. The mattress core 46 can be composed of a single type of material or a combination of materials and/or devices. In the case of a powered surface, the mattress core 46 includes at least one fluid bladder 54 therein that receives fluid from a fluid supply FS1 to maintain the fluid pressure within the fluid bladder 54 at a predetermined level. In some contemplated embodiments, the powered surface can include non-powered components, such as, a foam frame that at least one fluid bladder 54 is positioned between. In some contemplated embodiments, wedge shaped bladders are mirrored laterally about the centerline of the mattress MT1 and are configured to be inflated consecutively to laterally tilt the occupant, thereby relieving pressure on various portions of the occupant's body to help reduce the occurrences of pressure ulcers.

In the case of a non-powered mattress, the mattress core 46 is composed of a cellular engineered material, such as, single density foam. In some contemplated embodiments, the mattress core 46 includes at least one bladder 54, such as, a static air bladder or a static air bladder with foam contained there within, a metal spring and/or other non-powered support elements or combinations thereof. In some contemplated embodiments, the mattress core 46 and includes multiple zones with different support characteristics configured to enhance pressure redistribution as a function of the proportional differences of a person's body. Also, in some embodiments, the mattress core 46 includes various layers and/or sections of foam having different impression load deflection (ILD) characteristics, such as, in the NP100 Prevention Surface, AccuMax Quantum™ VPC Therapy Surface, and NP200 Wound Surfaces sold by Hill-Rom®.

The topper TP1 is positioned on the mattress and is used to regulate the amount heat and moisture produced by a person supported on the topper TP1. In some contemplated embodiments, the topper TP1 can be integrated into the mattress MT1. In some contemplated embodiments, the topper TP1 can be used to regulate the amount of heat and moisture present at or near the interface between the occupant supported on the topper TP1 and the topper TP1. In some contemplated embodiments, the topper TP1 is a low-air loss topper.

Low air-loss broadly refers to a feature of a support surface that provides a flow of air to assist in managing the heat and humidity of the skin. Two types of mechanisms that low air-loss support devices typically use to remove accumulated moisture and heat: convective evaporation and diffusive evaporation. Convective evaporation evaporates accumulated moisture by blowing air on the skin or drawing air away from the skin. In some contemplated embodiments, air can be blown on the skin through the upper surface of the topper TP1 that interfaces with the patient. In some contemplated embodiments, air can be drawn through the upper surface of the topper TP1 that interfaces with the patient and through the topper toward an exit by the fluid supply FS1. Diffusive evaporation evaporates accumulated moisture through and under the surface of the support device to cool the skin without blowing air directly thereon. One example of a diffusive device can be seen in FIG. 5 where the patient is lying on the topper in the supine position with fluid F1 flowing through the topper to remove heat H1 and moisture M1 radiated by the patient. In some contemplated embodiments, the low air-loss devices include a combination of diffusive and convective evaporation.

The topper TP1 includes a ticking TK1, an inlet IL1, a three-dimensionally engineered spacer SP1, and an outlet OL1. The ticking TK1 defines a chamber TC1 that the three-dimensionally engineered spacer SP1 is positioned within and is moisture permeable and air impermeable. In some contemplated embodiment, the ticking TK1 can be both moisture permeable and air permeable. In some contemplated embodiment, the mattress cover 44 and the ticking TK1 can be composed of the same material and have the same physical characteristics. The inlet IL1 is positioned along a side of the topper TP1 and allows for fluid to be communicated from the fluid supply FS1 into the chamber TC1.

The outlet OL1 is positioned along a side of the topper TP1 opposite the inlet IL1 and allows fluid entering the chamber TC1 through the inlet IL1 to pass through the chamber TC1 and exit the topper. In some contemplated embodiments, no vent is provided where air is able to be communicated through the upper surface of the topper TP1 that interfaces with the patient.

The spacer SP1 positioned within the chamber TC1 and helps maintain a path for the fluid from the fluid supply FS1 to flow through the chamber TC1 while a person is positioned thereon. In some contemplated embodiments, the three-dimensionally engineered spacer SP1 is composed of SpaceNet®, which is a product of Freudenberg. In other contemplated embodiments, the three-dimensionally engineered spacer 48 can be composed of other materials having a high fluid porosity and having some resistance against flattening. In some contemplated embodiments, the three-dimensionally engineered spacer SP1 includes at least one chamber and/or bladder (not shown) there within.

The fluid supply FS1 can be an air blower that can supply air to the mattress MT1 and topper TP1. The fluid supply FS1 can removably couple with the mattress MT1 and topper TP1 via a hose FH1. In some contemplated embodiments, fluid supply FS1 can also include a heating element (not shown) and/or a cooling element (not shown) that can heat and/or cool the fluid being supplied, and/or a filter (not shown) configured to filter the fluid being supplied.

The control system 16 is configured to assess and respond to adverse conditions that are detected. The control system 16 includes a processor 100, an input 102, and memory 104. In some contemplated embodiments, the input 102 is a sensor 106, such as, an image capture device or video camera, a 3D image sensor, a pressure sensor, a temperature sensor, an acoustic sensor, a force sensor, a moisture sensor, an accelerometer, a piezoelectric sensor, an ultrasonic sensor or other sensor configured to provide patient and environmental information to the processor 100 that is indicative of the status of a therapy, an identity of the person support surface being used, or a characteristic of the person, such as, the person's heart rate, respiration rate, respiration amplitude, skin temperature, weight, sleep state, body orientation, position, and/or other physiological characteristics or information about the person's condition. In some contemplated embodiments, the temperature, force, pressure, moisture, and ultrasonic sensors are incorporated into the mattress MT1 and/or topper TP1. In some contemplated embodiments, the accelerometer and piezoelectric sensors are coupled to garments, linens, or the person's skin. In some contemplated embodiments, the force, 3D image, and video sensors are coupled to the person support apparatus 12. In some contemplated embodiments, the 3D image, video and ultrasonic sensors are positioned in the room proximate to the person. In some contemplated embodiments, the sensors 106 are incorporated into the person support surface 14 or in a topper positioned on the person support surface 14, for example, as disclosed in U.S. Pat. No. 7,515,059 to Price et al., U.S. Patent Publication No. 2011/0068928 to Riley et al., and U.S. Patent Publication No. 2011/0024076 to Lachenbruch, et al. In some contemplated embodiments, the sensors 106 are positioned on the patient contacting surface of the topper TP1 or mattress MT1, in the chamber TC1, or in the ticking TK1. In some contemplated embodiments, the sensors 106 are load cells coupled to the upper frame 20. In some contemplated embodiments, the input 102 is a user interface 108 configured to receive information from a caregiver or other user. In some contemplated embodiments, the input 102 is a pressure mapping mat positioned on the person support surface 14. In some contemplated embodiments, the sensors 106 communicate wirelessly with the control system 16.

In some contemplated embodiments, friction and shear can be determined using a combination of the ultrasonic sensor, 3D image sensor, and/or image capture device and the pressure sensor and/or force sensor sensing the amount of pressure and force on the topper TP1 and the vertical and horizontal components of the movement of a person's body with respect to the surface. In one contemplated embodiment, if the coefficient of friction for the surface is known, the amount of friction the person experiences as a result of their weight can be calculated. In one contemplated embodiment, if the amount of the person has a small vertical component to their movement and their horizontal movement component is larger, the person may be experiencing a shear force. In some contemplated embodiments, the Doppler method can be used to measure the movement of the person, for example, their heart, with respect to the surface. In some contemplated embodiments, the stress on a person's skin can be calculated using the shear forces, the friction, the skin temperature, and the skin moisture level.

In some contemplated embodiments, the input 102 receives information from a remote database or system, such as, an Electronic Medical Record (EMR) system 110 or care facility record or information databases, in communication with the processor 100 via a care facility network 112. In some contemplated embodiments, the information includes, but is not limited to, risk assessments for the person, medical history, medications, Braden scores, health conditions, nutritional information for the person, assessed sensory perception information, staffing levels for the facility, care facility standard protocols, caregiver alarm preferences, agitation level of the person, and other information related to the person, caregiver, and care facility. In some contemplated embodiments, the processor 100 can output information, automatically or manually upon caregiver input, to the EMR for charting, which can include therapy initiation and termination, adverse event occurrence information, therapy protocol used, caregiver ID, and any other information associated with the occupant, caregiver, person support apparatus 12, person support surface 14, and adverse event.

The inputs 102 provide patient and environmental information that may include both spatial and temporal components and may relate to a variety of things, including, but not limited to, the person's current diagnosis, medications the person is taking, the person's physiological characteristics, the person's medical history, risk assessments performed by a caregiver, medical procedures the person has undergone, the status of medical equipment in the vicinity of the person or that is associated with the person (i.e., the person support apparatus 12 and the person support surface 14), care facility protocols and procedures, care facility logistics, caregiver or patient inputs, and other information about the person, medical devices, caregivers, and care facility that can be provided by an EMR or a patient activity log, gathered by and from the person support apparatus 12 and mattress MT1 and other medical devices assigned to the person, or through the care facility network.

The memory 104 stores one or more instruction sets configured to be executed by the processor 100 when the occupant egress prediction system 10 is armed. In some contemplated embodiments, the system 10 is armed manually by the caregiver or automatically based on information from the patient's EMR, the caregiver, and/or a protocol triggered by the risk profile of the patient. The instruction sets define procedures 114 that cause the processor 100 to implement one or more protocols that alert a caregiver via a communication system (not shown) when the system 10 detects or determines that a pressure ulcer has formed or may form over time if no intervention is implemented.

The communication system can be used to alert a caregiver proximate to the person support apparatus 14 (i.e., in the same room or in the hall way connected to the room) and a caregiver remote from the person support apparatus 14. In some contemplated embodiments, the communication system is a patient/nurse call system that can include patient stations capable of generating hospital calls and a remote master station which can prioritize and store the calls. One example of such a system is disclosed in U.S. Pat. No. 5,561,412 issued on Oct. 1, 1996 to Novak et al., which is incorporated by reference herein in its entirety. Another example of such a system is disclosed in U.S. Pat. No. 4,967,195 issued on May 8, 2006 to Shipley, which is incorporated by reference herein in its entirety. In another illustrative embodiment, the communication system can include a status board that displays the alert. The communication system can alert the caregiver by posting the alert to a status board, using a nurse call system, directly contacting the caregiver on their phone or pager, providing a local alert over the facility PA system, and opening a connection that allows the caregiver to speak directly to the patient. The communication can also escalate the vigilance monitoring of the patient.

In another contemplated embodiment, the communication system is a system for transmitting voice and data in packets over a network with any suitable number of intra-room networks that can couple a number of data devices to an audio station, where the audio station couples the respective intra-room network to a packet based network. One example of such a system is disclosed in U.S. Pat. No. 7,315,535 issued on Jan. 1, 2008 to Schuman, which is incorporated by reference herein in its entirety. Another example of such a system is disclosed in U.S. Patent Publication No. 2008/0095156 issued on Apr. 24, 2008 to Schuman, which is incorporated by reference herein in its entirety.

In yet another contemplated embodiment, the communication system is included a patient/nurse call system, a nurse call/locating badge, an electronic medical record (EMR) database, and one or more computers programmed with work-flow process software. One example of such a system is disclosed in U.S. Patent Publication No. 2008/0094207 published on Apr. 24, 2008 to Collins, J R. et al., which is incorporated by reference herein in its entirety. Another example of such a system is disclosed in U.S. Patent Publication No. 2007/0210917 published on Sep. 13, 2007 to Collins, J R. et al., which is incorporated by reference herein in its entirety. Yet another example of such a system is disclosed in U.S. Pat. No. 7,319,386 published on Jan. 15, 2008 to Collins, J R. et al., which is incorporated by reference herein in its entirety. It should be appreciated that the work-flow process software can be the NaviCare® software available from Hill-Rom Company, Inc. It should also be appreciated that the work-flow process software can be the system disclosed in U.S. Pat. No. 7,443,303 issued on Oct. 28, 2008 to Spear et al., which is incorporated by reference herein in its entirety. It should further be appreciated that the badge can be of the type available as part of the ComLinx™ system from Hill-Rom Company, Inc. It should also be appreciated that the badge can also be of the type available from Vocera Communications, Inc.

In still another contemplated embodiment, the communication system is configured to organize, store, maintain and facilitate retrieval of bed status information, along with the various non-bed calls placed in a hospital wing or ward, and remotely identify and monitor the status and location of the person support apparatus, patients, and caregivers. One example of such a system is disclosed in U.S. Pat. No.

7,242,308 issued on Jul. 10, 2007 to Ulrich et al., which is incorporated by reference herein in its entirety. It should be appreciated that the remote status and location monitoring can be the system disclosed in U.S. Pat. No. 7,242,306 issued on Jul. 10, 2007 to Wildman et al., which is incorporated by reference herein in its entirety. It should also be appreciated that the remote status and location monitoring can be the system disclosed in U.S. Patent Publication No. 2007/0247316 published on Oct. 25, 2007 to Wildman et al., which is incorporated by reference herein in its entirety.

In one contemplated embodiment, the instruction set defines a procedure 114 that causes the processor 100 to send the caregiver an alert via a communication system (not shown) and/or activate a therapy upon determining that skin breakdown has occurred or is predicted to occur based on the information from the inputs 102. Procedure 114 begins with step 116 in which the processor 100 receives patient and environmental information from the input 102. In one example, the information from the input 102 includes information used to populate a Braden score table. In other examples, the information includes indicated in the table below:

| Sensory Perception (ability to respond meaningfully to pressure-related discomfort) | Moisture (degree to which skin is exposed to moisture) | Activity (degree of physical activity) | Mobility (ability to change and control body position) | Nutrition (usual food intake pattern) | Friction & Shear |
|---|---|---|---|---|---|
| 1. Completely Limited (unresponsive to painful stimuli, due to diminished level of consciousness or sedation, or limited ability to feel pain over most of the body) | 1. Constantly Moist (skin is kept moist almost constantly by perspiration, urine, etc. Dampness is detected every time patient is moved or turned) | 1. Confined to bed. | 1. Completely Immobile (does not make even slight changes in body or extremity position without assistance) | 1. Very Poor (never eats a complete meal. Rarely eats more than a of any food offered. Eats 2 servings or less of protein (meat or dairy products) per day. Takes fluids poorly. Does not take a liquid dietary supplement, or is NPO and/or maintained on clear liquids or IV = s for more than 5 days) | 1. Problem (requires moderate to maximum assistance in moving. Complete lifting without sliding against sheets is impossible. Frequently slides down in bed or chair, requiring frequent repositioning with maximum assistance. Spasticity, contractures or agitation leads to almost constant friction) |
| 2. Very Limited (responds only to painful stimuli. Cannot communicate discomfort except by moaning or restlessness, or has a sensory impairment which limits the ability to feel pain or discomfort over ½ of the body) | 2. Very Moist (skin is often, but not always moist. Linen must be changed at least once a shift) | 2. Chairfast (ability to walk severely limited or non-existent. Cannot bear own weight and/or must be assisted into chair or wheelchair) | 2. Very Limited (makes occasional slight changes in body or extremity position but unable to make frequent or significant changes independently) | 2. Probably Inadequate (rarely eats a complete meal and generally eats only about 2 of any food offered. Protein intake includes only 3 servings of meat or dairy products per day. Occasionally will take a dietary Supplement, or receives less than optimum amount of liquid diet or tube feeding) | 2. Potential Problem (moves feebly or requires minimum assistance. During a move skin probably slides to some extent against sheets, chair, restraints or other devices. Maintains relatively good position in chair or bed most of the time but occasionally slides down) |
| 3. Slightly Limited (responds to verbal commands, but cannot always communicate discomfort or the need to be turned, or has some sensory impairment which limits ability to feel pain or discomfort in 1 or 2 extremities) | 3. Occasionally Moist: (skin is occasionally moist, requiring an extra linen change approximately once a day) | 3. Walks Occasionally (walks occasionally during day, but for very short distances, with or without assistance. Spends majority of each shift in bed or chair) | 3. Slightly Limited (makes frequent though slight changes in body or extremity position independently) | 3. Adequate (eats over half of most meals. Eats a total of 4 servings of protein (meat, dairy products per day. Occasionally will refuse a meal, but will usually take a supplement when offered, or is on a tube feeding or TPN regimen which probably meets most of nutritional needs) | 3. No Apparent Problem (moves in bed and in chair independently and has sufficient muscle strength to lift up completely during move. Maintains good position in bed or chair) |
| 4. No Impairment (responds to verbal commands. Has no sensory deficit which would limit ability to feel or voice pain or discomfort) | 4. Rarely Moist (skin is usually dry, linen only requires changing at routine intervals) | 4. Walks Frequently (walks outside room at least twice a day and inside room at least once every two hours during waking hours) | 4. No Limitation (makes major and frequent changes in position without assistance) | 4. Excellent (eats most of every meal. Never refuses a meal. Usually eats a total of 4 or more servings of meat and dairy products. Occasionally eats between meals. Does not require supplementation) | |
| Scores | | | | | Total Score |

In other examples, the information includes the status of a therapy, an identity of the person support surface being used, or a characteristic of the person, such as, the person's heart rate, respiration rate, respiration amplitude, skin temperature, weight, sleep state, body orientation, position, and/or other physiological characteristics or information about the person's condition, the person's current diagnosis, medications the person is taking, the person's physiological characteristics, the person's medical history, risk assessments performed by a caregiver, medical procedures the person has undergone, the status of medical equipment in the vicinity of the person or that is associated with the person (i.e., the person support apparatus 12 and the person support surface 14), care facility protocols and procedures, care facility logistics, caregiver or patient inputs and other information about the person, medical devices, caregivers, and care facility that can be provided by an EMR or a patient activity log, gathered by and from the person support apparatus 12 and mattress MT1 and other medical devices assigned to the person, or through the care facility network.

In step 118, the processor 100 inputs the information into a table, such as, a Braden score table. It should be appreciated that this step is not necessary for instances where a score table is not desired or needed.

In step 120, the processor 100 determines what the level of risk of skin breakdown as a function of the inputs. In one contemplated embodiment, the processor calculates a risk score based on the Braden score table. In one example, if the amount of moisture sensed is high (2), the person's level of activity is medium (3), they don't eat often (2), and the person is able to reposition themselves easily (3,3), the person may have a moderate risk of developing a pressure ulcer based on the Braden score table. In another contemplated embodiment, the processor 100 compares the inputs to predetermined thresholds. In some contemplated embodiments, the thresholds are set by the facility care protocol. In another contemplated embodiment, the thresholds are set based on a caregiver assessment, a data set, which can specify thresholds based on the person's age, sex, weight, height and other information, or based on the person's history, which can take into account whether the person is a diabetic or is on medication that may affect the skin temperature and moisture levels. In another contemplated embodiment the threshold can be the last set of inputs received or the last caregiver assessment. In some contemplated embodiments, certain information may not be considered or given less weight based on information about the patient. For example, pressure readings may not be considered for children, but incontinence is given more weight.

Once the level of risk is determined, the processor 100 determines whether an intervention is required. In one contemplated embodiment, the processor examines the hospital protocol in step 122 and determines what procedures are prescribed by the protocol. One example may be to activate a low air loss therapy by activating the fluid supply FS1 and communicating air through the topper TP1 to remove excess moisture and heat from the skin. Another example may be to activate a lateral rotation therapy to rotate the person from side to side. Another example may be the caregiver applying a salve to the person's skin. In some contemplated embodiments, the therapy is configured to maintain the person's skin within a predefined range.

In step 124, the processor 100 notifies the caregiver and/or activates a therapy. If the caregiver is notified, the notification can include information about the current condition of the person and recommended interventions based on the care facility protocols. If the therapy is activated, the processor 100 monitors the inputs 102 to adjust the therapy to maintain the person with in a predetermined range of values. In some contemplated embodiments, the processor can receive information that causes the processor to deactivate the therapy or notify the caregiver that an intervention is no longer necessary. In one example, if the caregiver is notified that the person needs to be turned and the person turns themselves in the meantime, the caregiver can be notified that the person no longer needs to be turned. In another example, if a therapy is scheduled to run, such as, heat and moisture regulation therapy, and the person's skin temperature and moisture levels are within a predetermined range, the therapy can be delayed, rescheduled, or stopped.

Many other embodiments of the present disclosure are also envisioned. For example, a method comprises receiving an input indicative of a factor that contribute to the development of pressure ulcers; comparing the input to a predetermined threshold; and if the input exceeds the threshold, notifying a caregiver that a pressure ulcer may develop. In one contemplated embodiment, input includes at least one of the interface pressure, the skin temperature, the skin moisture level, presence of tissue damage, incontinence, presence of a pressure ulcer, lack of motion, lack of activity, presence of shear forces, presence of friction forces, and use of therapies. In another contemplated embodiment, the input includes at least one of a spatial and temporal component related to the factor. In another contemplated embodiment, the spatial component identifies the location where the factor was detected. In another contemplated embodiment, the temporal component identifies the duration the factor was detected. In another contemplated embodiment, the input includes information received from an electronic medical record system. In another contemplated embodiment, the input includes information indicative of the patient's risk for skin breakdown. In another contemplated embodiment, the input includes information indicative of the patient's medical history. In another contemplated embodiment, the input includes information indicative of the patient's Braden score. In another contemplated embodiment, the input includes information indicative of the medication the patient is taking. In another contemplated embodiment, the method further comprising the step of receiving a second input corresponding to an institutional care protocol. In another contemplated embodiment, the institutional care protocol includes at least one of an instruction to use a specialty surface, an instruction to use a heat and moisture regulating therapy, an instruction to use a catheter, an instruction to rotate the patient, and an instruction to initiate a patient turning therapy.

In another example, a method comprises receiving an input indicative of a factor that contribute to the development of pressure ulcers; comparing the input to a predetermined threshold; and if the input exceeds the threshold, activating a therapy configured to reduce the magnitude of the input. In one contemplated embodiment, the therapy includes a patient turning therapy. In another contemplated embodiment, the therapy includes continuous lateral rotation therapy. In another contemplated embodiment, the therapy includes a heat and moisture regulating therapy. In another contemplated embodiment, the therapy includes a low air loss therapy. In another contemplated embodiment, the therapy includes a targeted cooling. In another contemplated embodiment, the therapy includes targeted repositioning. In another contemplated embodiment, the therapy includes a patient turning therapy. In another contemplated embodiment, the method further comprising the step of reporting compliance with an institutional care protocol. In another contemplated embodiment, the therapy includes delivery of a pH neutralizing solution.

In another example, a method comprises receiving an input indicative of a factor that contribute to the development of pressure ulcers; determining a Braden score of a person as a function of the input; comparing the Braden score to a predetermined threshold; and if the input exceeds the threshold, activating a therapy configured to reduce the magnitude of the input.

In another example, a method comprises receiving a first input indicative of a factor that contribute to the development of pressure ulcers; receiving a second input indicative of a factor that contribute to the development of pressure ulcers a predetermined time after receiving the first input; determining the difference between the first input and the second input; if the difference indicates an increase in the factor that contributes to the development of pressure ulcers, activating a therapy configured to reduce the magnitude of the factor.

In another example, a method comprises receiving a first input indicative of a factor that contribute to the development of pressure ulcers; receiving a second input indicative of a factor that contribute to the development of pressure ulcers a predetermined time after receiving the first input; determining a first Braden score as a function of the first input; determining a second Braden score as a function of the second input; comparing the first Braden score to the second Braden score; and if the first Braden score is less than the second Braden score, activating a therapy configured to reduce the magnitude of the factor.

In another example, a method comprises receiving a first input indicative of a factor that contribute to the development of pressure ulcers; receiving a second input indicative of a factor that contribute to the development of pressure ulcers a predetermined time after receiving the first input; determining a first Braden score as a function of the first input; determining a second Braden score as a function of the second input; comparing the first Braden score to the second Braden score; and if the first Braden score is less than the second Braden score, notify a caregiver.

In another example, a method comprises receiving an first input indicative of a characteristic of a patient; receiving a second input indicative of at least one factor that contributes to the development of pressure ulcers, wherein at least one of the at least one factor is ignored as a function of the first input; comparing the second input to a predetermined threshold; if the difference indicates an increase in the factor that contributes to the development of pressure ulcers, at least one of activating a therapy configured to reduce the magnitude of the factor and notifying a caregiver.

In another example, a method comprises receiving an input indicative of at least one factor that contributes to the development of pressure ulcers; determining a risk score as a function of the input; comparing the risk score to a previous risk score; and at least one of activating a therapy configured to reduce the magnitude of the factor and notifying a caregiver if the risk score is greater than the previous risk score.

In another example, a method comprises receiving an input indicative of at least one factor that contributes to the development of pressure ulcers; determining a risk score as a function of the input; comparing the risk score to a previous risk score; and at least one of activating a therapy configured to reduce the magnitude of the factor and notifying a caregiver if magnitude of the difference is greater than a predetermined threshold.

In another example, a method comprises receiving an input indicative of at least one factor that contributes to the development of pressure ulcers; determining a risk score as a function of the input; receiving a second input indicative of at least one factor that contributes to the development of pressure ulcers; determining a second risk score as a function of the second input; comparing the second risk score to the risk score; and at least one of activating a therapy configured to reduce the magnitude of the factor and notifying a caregiver if the magnitude of the difference between the scores is greater than a predetermined threshold.

In another example, a method comprises receiving an input indicative of at least one factor that contributes to the development of pressure ulcers; determining a risk score as a function of the input; comparing the risk score to a previous risk score; and at least one of activating a therapy configured to reduce the magnitude of the factor and notifying a caregiver if the rate of change between the risk score and the previous risk score is greater than a predetermined threshold.

In another example, a method of predicting the occurrence of a pressure ulcer comprises the steps of: receiving a first input signal indicative of a physiological characteristic of a person supported on a person support structure; receiving a second input signal indicative of at least one of a pressure ulcer risk assessment and a pressure ulcer history of a person; comparing the first input signal to a predetermined threshold; if the first input signal exceeds the predetermined threshold and the second input signal indicates at least one of at least a moderate risk and a history of pressure ulcers, generating an alert. In one contemplated embodiment, the physiological characteristic includes interface pressure experienced by a person's skin. In another contemplated embodiment, the physiological characteristic includes a person's skin temperature. In another contemplated embodiment, the physiological characteristic includes a person's skin moisture level. In another contemplated embodiment, the physiological characteristic includes the presence of an incontinence condition. In another contemplated embodiment, the physiological characteristic includes an amount of shear experienced by a person's skin. In another contemplated embodiment, the physiological characteristic includes an amount of friction experienced by a person's skin. In another contemplated embodiment, the physiological characteristic includes the location on a person's body that the physiological characteristic corresponds to. In another contemplated embodiment, the pressure ulcer risk assessment is input by a caregiver via an input on the person support structure. In another contemplated embodiment, the pressure ulcer risk assessment information is received from an electronic medical record database. In another contemplated embodiment, the pressure ulcer history information is received from an electronic medical record database. In another contemplated embodiment, the pressure ulcer risk assessment includes a Braden score. In another contemplated embodiment, the pressure ulcer risk assessment includes a person's diagnosed condition. In another contemplated embodiment, the pressure ulcer risk assessment includes a person's current medication side effects. In another contemplated embodiment, the pressure ulcer risk assessment includes a therapy status. In another contemplated embodiment, the pressure ulcer risk assessment includes a mattress type. In another contemplated embodiment, a therapy is activated if the first input signal exceeds the predetermined threshold and the second input signal indicates at least of at least a moderate risk and a history of pressure ulcers. In another contemplated embodiment, the therapy includes continuous lateral rotation. In another contemplated embodiment, the therapy includes low air loss therapy. In another contemplated embodiment, the therapy is directed toward the location where the pressure ulcer is predicted to occur.

In another example, a method of predicting an occurrence of a pressure ulcer comprises the steps of: receiving a first input signal indicative of a physiological characteristic of a person at a first time; receiving a second input signal indicative of the physiological characteristic at a second time; determining if a pressure ulcer is likely to occur based on the first input signal and the second input signal; and generating an intervention if a pressure ulcer is likely to occur. In one contemplated embodiment, the physiological characteristic includes at least one of an interface pressure, a skin temperature, a skin moisture level, an amount of shear, an amount of friction, an incontinence condition, and a location that the physiological characteristic corresponds to. In another contemplated embodiment, a pressure ulcer is likely to occur when the difference between the first input signal and the second input signal indicates that the characteristic is increasing over time. In another contemplated embodiment, a pressure ulcer is likely to occur when the physiological characteristic exceeds a predetermined threshold for a predetermined period of time. In another contemplated embodiment, the intervention includes activating a therapy. In another contemplated embodiment, the therapy includes at least one of rotational therapy and low air loss therapy. In another contemplated embodiment, the therapy is directed toward the location where the pressure ulcer is predicted to occur. In another contemplated embodiment, the intervention includes alerting a caregiver.

In another example, a control system comprises: an input configured to receive information corresponding to at least two of a physiological characteristic of a person, a pressure ulcer risk assessment, and a medical history of a person; a processor; and a memory unit including instructions configured to be executed by the processor, the instructions, when executed by the processor, causing the processor to at least one of activate a therapy on a person support structure and generate an alert. In one contemplated embodiment, the physiological characteristic includes an interface pressure. In another contemplated embodiment, the physiological characteristic includes a skin temperature. In another contemplated embodiment, the physiological characteristic includes a person's skin moisture level. In another contemplated embodiment, the physiological characteristic includes the presence of an incontinence condition. In another contemplated embodiment, the physiological characteristic includes an amount of shear experienced by a person's skin. In another contemplated embodiment, the physiological characteristic includes an amount of friction experienced by a person's skin. In another contemplated embodiment, the physiological characteristic includes the location on a person's body that the physiological characteristic corresponds to. In another contemplated embodiment, the pressure ulcer risk assessment is input by a caregiver via an input on the person support structure. In another contemplated embodiment, the pressure ulcer risk assessment information is received from an electronic medical record database. In another contemplated embodiment, the pressure ulcer history information is received from an electronic medical record database. In another contemplated embodiment, the pressure ulcer risk assessment includes a Braden score. In another contemplated embodiment, the pressure ulcer risk assessment includes a person's diagnosed condition. In another contemplated embodiment, the pressure ulcer risk assessment includes a person's current medication side effects. In another contemplated embodiment, the pressure ulcer risk assessment includes a therapy status. In another contemplated embodiment, the pressure ulcer risk assessment includes a mattress type. In another contemplated embodiment, a therapy is activated if the first input signal exceeds the predetermined threshold and the second input signal indicates at least of at least a moderate risk and a history of pressure ulcers. In another contemplated embodiment, the therapy includes continuous lateral rotation. In another contemplated embodiment, the therapy includes low air loss therapy. In another contemplated embodiment, the therapy is directed toward the location where the pressure ulcer is predicted to occur.

In another example, a control system comprises: an input; a processor configured to receive information from the input corresponding to at least two of a characteristic of a person, a pressure ulcer risk, and a medical history of a person; and a memory unit including instructions configured to be executed by the processor, the instructions, when executed by the processor, cause the processor to determine when a pressure ulcer will likely occur based on the information received from the input, and generate an intervention if a pressure ulcer will likely occur. In one contemplated embodiment, the characteristic includes at least one of an interface pressure, a skin temperature, a skin moisture level, the presence of an incontinence condition, a shear force, a friction force, and a location on a person's body that the characteristic corresponds to. In another contemplated embodiment, the pressure ulcer risk is input by a caregiver. In another contemplated embodiment, the pressure ulcer risk is received from an electronic medical record database. In another contemplated embodiment, the pressure ulcer history information is received from an electronic medical record database. In another contemplated embodiment, the pressure ulcer risk includes at least one of a pressure ulcer risk score, a diagnosed condition, a side effect of a current medication, a therapy status, and a mattress type. In another contemplated embodiment, the intervention includes activating a therapy. In another contemplated embodiment, the therapy is activated if the first input signal exceeds the predetermined threshold and the second input signal indicates at least of at least a moderate risk and a history of pressure ulcers. In another contemplated embodiment, the therapy includes at least one of a rotational therapy and a low air loss therapy. In another contemplated embodiment, the therapy is directed toward the location where the pressure ulcer is predicted to occur. In another contemplated embodiment, the intervention includes alerting a caregiver. In another contemplated embodiment, the alert is communicated through a nurse call system. In another contemplated embodiment, the alert is generated if the characteristic exceeds a predetermined threshold for a predetermined period of time and at least one of the pressure ulcer risk indicates at least a moderate risk and the pressure ulcer history indicates a history of a pressure ulcers. In another contemplated embodiment, the pressure ulcer risk is determined by populating a risk assessment table with information that is at least one of sensed by a sensing device and received from an electronic medical record.

In another example, a method of predicting the occurrence of a pressure ulcer, comprising the steps of: receiving a first input indicative of a physiological characteristic of a person supported on a person support structure at a first time; receiving a second input indicative of at least one of a pressure ulcer risk assessment and a pressure ulcer history of a person; determining if a pressure ulcer is likely to occur based on the first input and the second input; if a pressure ulcer is likely to occur, at least one of activating a therapy and alerting a caregiver. In one contemplated embodiment, the alert is generated if the physiological characteristic exceeds a predetermined threshold for a predetermined period of time and at least one of the pressure ulcer risk indicates at least a moderate risk and the pressure ulcer history indicates a history of a pressure ulcers. In another contemplated embodiment, the therapy includes at least one of a rotation therapy and a low air loss therapy. In another contemplated embodiment, the therapy is directed toward the location where the pressure ulcer is predicted to occur.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. A method of operating a patient support apparatus to predict and mitigate an occurrence of a pressure ulcer, comprising the steps of:
    receiving from a sensor of the patient support apparatus a first input signal indicative of a physiological characteristic of a person at a first time;
    receiving from the sensor of the patient support apparatus a second input signal indicative of the physiological characteristic of the person at a second time;
    determining a difference between the first input signal and the second input signal;
    receiving information from a medical device that is separate from the patient support apparatus and is associated with the person;
    processing the difference between the first and second input signals and the information received from the medical equipment device to determine if a pressure ulcer is likely to occur based on a trend indicated by the difference between the first input signal and the second input signal and the information received from medical equipment device;
    if a pressure ulcer is likely to occur, automatically generating a signal to activate a therapy to mitigate a condition causing the likelihood of the pressure ulcer;
    receiving from the sensor of the patient support apparatus a third input signal indicative of the physiological characteristic of the person at a third time that is after the first time and the second time;
    determining a difference between the third input signal and at least one of the first input signal and second input signal; and
    generating a signal to modify the therapy based on the difference between the third input signal and at least one of the first input signal and second input signal;
    wherein the physiological characteristic includes at least one physiological factor that contributes to skin breakdown.

2. The method of claim 1, wherein the physiological characteristic that contributes to skin breakdown includes at least one of an interface pressure, a skin temperature, a skin moisture level, an amount of shear, an amount of friction, and an incontinence condition.

3. The method of claim 1, wherein a pressure ulcer is likely to occur when the trend indicates that the physiological characteristic is increasing over time.

4. The method of claim 1, wherein a pressure ulcer is likely to occur when the trend indicates that the physiological characteristic exceeds a predetermined threshold for a predetermined period of time.

5. The method of claim 1, wherein the therapy includes at least one of rotational therapy and low air loss therapy.

6. The method of claim 1, wherein the therapy is directed toward a location where the pressure ulcer is predicted to occur.

7. The method of claim 1, wherein automatically generating the signal further includes alerting a caregiver.

8. A control system of a patient support apparatus, comprising:
    an input;
    a processor configured to receive (i) information from the input corresponding to a change in at least two physiological characteristics of a person, (ii) information related to a pressure ulcer risk and a medical history of a person, and (iii) information from a medical device that is separate from the patient support apparatus and is associated with the person; and
    a memory unit including instructions configured to be executed by the processor, the instructions, when executed by the processor, cause the processor to determine if a pressure ulcer will likely occur based on the information received from the input, the information related to a pressure ulcer risk, a medical history of a person, and the medical equipment device, and automatically generate a signal to activate a therapy if a pressure ulcer will likely occur; wherein the memory unit further includes instructions that, when executed by the processor cause the processor to:
    receive an input signal indicative of a physiological characteristic of the person after the signal to activate the therapy has been generated;
    determine that the input signal after signal to activate a therapy has been generated represents a change in one of the at least two physiological characteristics of a person; and generate a signal to modify the therapy based on the change in the physiological characteristic.

9. The control system of claim 8, wherein the physiological characteristics of a person includes at least one of an interface pressure experienced by the person's skin, a skin temperature, a skin moisture level, the presence of an incontinence condition, a shear force experienced by the person's skin, a friction force experienced by the person's skin.

10. The control system of claim 8, wherein the pressure ulcer risk is input by a caregiver.

11. The control system of claim 8, wherein the pressure ulcer risk is received from an electronic medical record database.

12. The control system of claim 8, wherein the medical history of the person is received from an electronic medical record database.

13. The control system of claim 8, wherein the pressure ulcer risk includes at least one of a pressure ulcer risk score, a diagnosed condition, a side effect of a current medication, a therapy status, and a mattress type.

14. The control system of claim 8, wherein the therapy is activated if (i) at least one of the physiological characteristics of the person exceeds a predetermined threshold, (ii) at least one of the pressure ulcer risk indicates a moderate or higher risk, and (iii) the medical history indicates a history of pressure ulcers.

15. The control system of claim 8, wherein the therapy includes at least one of a rotational therapy and a low air loss therapy.

16. The control system of claim 8, wherein the therapy is directed toward a location where the pressure ulcer is predicted to occur.

17. The control system of claim 8, wherein the instructions causes the processor to automatically generate the signal further includes alerting a caregiver.

18. The control system of claim 17, wherein the alert is communicated through a nurse call system.

19. The control system of claim 17, wherein the alert is generated if (i) at least one of the physiological characteristics exceeds a predetermined threshold for a predetermined period of time, (ii) at least one of the pressure ulcer risk indicates a moderate or higher risk, and (iii) the pressure ulcer history indicates a history of a pressure ulcers.

20. The control system of claim 8, wherein the pressure ulcer risk is determined by populating a risk assessment table with information received from the input that is at least one of sensed by a sensing device and received from an electronic medical record.

21. A method of operating a patient support apparatus to predict and mitigate an occurrence of a pressure ulcer, comprising the steps of:

receiving from a sensor of the patient support apparatus a first input signal indicative of a physiological characteristic of a person at a first time;

receiving from the sensor of the patient support apparatus a second input signal indicative of the physiological characteristic of the person at a second time;

determining a difference between the first input signal and the second input signal;

processing the difference between the first and second input signals to determine if a pressure ulcer is likely to occur based on a trend indicated by the difference between the first input signal and the second input signal;

if a pressure ulcer is likely to occur, automatically generating a signal to activate a therapy to mitigate a condition causing the likelihood of the pressure ulcer;

receiving from the sensor of the patient support apparatus a third input signal indicative of the physiological characteristic of the person at a third time that is after the first time and the second time;

determining a difference between the third input signal and at least one of the first input signal and second input signal; and generating a signal to modify the therapy based on the difference between the third input signal and at least one of the first input signal and second input signal;

wherein the physiological characteristic includes at least one physiological factor that contributes to skin breakdown.

22. The method of claim 21, wherein the physiological characteristic that contributes to skin breakdown includes at least one of an interface pressure, a skin temperature, a skin moisture level, an amount of shear, an amount of friction, and an incontinence condition.

23. The method of claim 21, wherein a pressure ulcer is likely to occur when the trend indicates that the physiological characteristic is increasing over time.

24. The method of claim 21, wherein a pressure ulcer is likely to occur when the trend indicates that the physiological characteristic exceeds a predetermined threshold for a predetermined period of time.

25. The method of claim 21, wherein the therapy includes at least one of rotational therapy and low air loss therapy.

26. The method of claim 21, wherein the therapy is directed toward a location where the pressure ulcer is predicted to occur.

27. The method of claim 21, wherein automatically generating the signal further includes alerting a caregiver.

* * * * *

UNITED STATES PATENT AND TRADEMARK OFFICE
CERTIFICATE OF CORRECTION

PATENT NO. : 9,861,550 B2
APPLICATION NO. : 13/900209
DATED : January 9, 2018
INVENTOR(S) : David L. Ribble et al.

Page 1 of 1

It is certified that error appears in the above-identified patent and that said Letters Patent is hereby corrected as shown below:

On the Title Page

References Cited, Page 2, Column 2, Line 54 add the citation --2011/0301432 A1 12/2011 Riley--.

Signed and Sealed this
Tenth Day of July, 2018

Andrei Iancu
*Director of the United States Patent and Trademark Office*